United States Patent [19]

Morioka et al.

[11] Patent Number: 5,496,823
[45] Date of Patent: Mar. 5, 1996

[54] PHARMACEUTICAL COMPOSITION FOR INCREASING BLADDER CAPACITY

[75] Inventors: Yuko Morioka; Mitsuru Takano, both of Saitama, Japan

[73] Assignee: Hoechst Japan Limited, Tokyo, Japan

[21] Appl. No.: 287,794

[22] Filed: Aug. 9, 1994

Related U.S. Application Data

[63] Continuation of Ser. No. 986,903, Dec. 8, 1992, abandoned.

[30] Foreign Application Priority Data

Dec. 10, 1991 [JP] Japan .................................... 3-325458

[51] Int. Cl.$^6$ .................................................. A61K 31/52
[52] U.S. Cl. .......................................... 514/263; 514/264
[58] Field of Search ..................................... 514/263, 264

[56] References Cited

U.S. PATENT DOCUMENTS 4,289,776  9/1981  Mohler et al. .......................... 424/253

OTHER PUBLICATIONS

Drugs of the Future, vol. VII, No. 2, 1982, "Propentofgylline", pp. 119–120.
Morikawa et al., Pharmacometrics, vol. 37, No. 1, pp. 27–37 (1989).
Journal of New Remedies & Clinics (Shin–yaku to Rinsho) vol. 38 No. 12, pp. 133–138 (Dec. 1989), Kimura et al.
Pharmacometrics (Oyu Yakuri) vol. 30, No. 4, pp. 661–676 (p. 661, summary item 2 and p. 673 tables 13 and 14), Sakurai et al., 1985.
Chemical Abstracts 95(23):197310s, 1981.
Chemical Abstracts 110(15):128285d, 1988.
Chemical Abstracts 116(21):209267a, 1991.
Goodman Gilman et al. "The Pharmacological Basis of Therapeutics" (6th Ed.) New York, MacMillan Publishing, 1980, pp. 924–925.

*Primary Examiner*—Marianne M. Cintins
*Assistant Examiner*—M. Moezie
*Attorney, Agent, or Firm*—Finnegan, Henderson, Farabow, Garrett & Dunner

[57] ABSTRACT

Pharmaceutical compositions for the improvement of dysuria comprising a pharmaceutical carrier and a therapeutically effective amount of a xanthine derivative represented by the general formula I

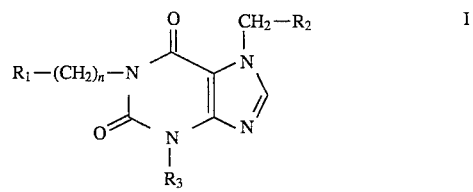

wherein $R_1$ denotes a group of the formula $R_4$-CO- or $R_5R_6$(OH)C- or a carboxyl group, wherein $R_4$ and $R_5$ independently denote an alkyl group having 1–3 carbon atoms, and $R_6$ denotes a hydrogen atom or an alkyl group having 1–3 carbon atoms, $R_2$ denotes a hydrogen atom, an alkyl group having 1–5 carbon atoms or an alkyloxy group having 1–5 carbon atoms, $R_3$ denotes an alkyl group having 1–3 carbon atoms and n denotes 1–6 or a pharmaceutically acceptable acid addition salt thereof.

They are active in prolonging urination intervals and increasing urination threshold pressure with almost no influence upon constrictive force of the bladder. Thus, they are effective in treatment and prevention of dysuria such as pollakiuria and incontinence of urine.

3 Claims, No Drawings

PHARMACEUTICAL COMPOSITION FOR INCREASING BLADDER CAPACITY

This application is a continuation of application Ser. No. 07/986,903 filed Dec. 8, 1992, now abandoned.

BACKGROUND OF THE INVENTION

1. Field of the Invention

This invention relates to novel pharmaceutical compositions for the improvement of dysuria such as pollaki-uria or incontinence of urine. Dysuria is often caused by adult diseases such as cerebrovascular disorders and prostatic diseases, which results in not only serious hamper of the patients' action in their daily life but also impairment of the patients' dignity. On the other hand, it gives a great burden on the nursing family. As the world becomes more aged in population, and also from the viewpoint of quality of life, development of agents for the improvement of dysuria with more definite efficacy and higher safety is highly desired. The compositions according to the invention are useful as a therapeutic agent with higher safety in dysuria such as pollakiuria and incontinence of urine.

2. Description of the Prior Art

Pharmaceutical compositions for the treatment of pollakiuria and incontinence of urine in urology include cholinolytics, antimuscarinics and calcium antagonists. None of such composition may be satisfactory either in efficacy or in adverse reaction. For example, whereas, cholinolytics typical of which is butylscopolamine are observed to be inhibitory on cystic smooth muscles, their use is associated with disadvantages in that they are also highly active on other cholinergic viscera such as digestive tracts, cardiac muscles, sialaden and pupillary muscles. Since treatment for dysuria needs a long period of time for continued use of a drug even in aged patients, it should not only be therapeutically highly effective but also be highly safe.

SUMMARY OF THE INVENTION

This invention is directed to pharmaceutical compositions for the improvement of dysuria comprising a pharmaceutical carrier and a therapeutically effective amount of a xanthine derivative represented by the formula (I)

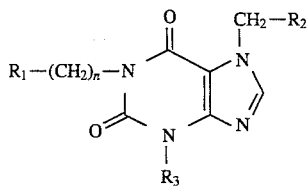

wherein $R_1$ denotes a group of the formula $R_4$-CO- or $R_5R_6(OH)C$- or a carboxyl group, wherein $R_4$ and $R_5$ independently denote an alkyl group having 1–3 carbon atoms, and $R_6$ denotes a hydrogen atom or an alkyl group having 1–3 carbon atoms, $R_2$ denotes a hydrogen atom, an alkyl group having 1–5 carbon atoms or an alkyloxy group having 1–5 carbon atoms, $R_3$ denotes an alkyl group having 1–3 carbon atoms and n denotes 1–6 or a pharmaceutically acceptable acid addition salt thereof, wherein 3,7-dihydro-3-methyl- 1 -(5-oxohexyl)-7-methyl-1H-purine-2,6-dione is excluded.

In the definition of the substituents in the formula (I), the alkyl group having 1–3 carbon atoms includes methyl, ethyl or n-propyl, and the alkyl group having 1–5 carbon atoms includes methyl, ethyl, n-propyl, iso-propyl, n-butyl, iso-butyl, n-pentyl or the like.

Preferred compounds of the formula I are those in which $R_4$ is a methyl group, or $R_5$ is a methyl group and $R_6$ is a hydrogen atom or a methyl group, or $R_2$ is ethoxy, ethyl or a hydrogen atom, or n is 4.

A further object of the invention is the use of a xanthine derivative represented by $CH_2$ the general formula I

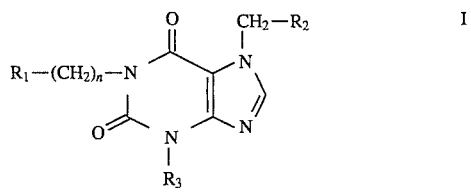

wherein $R_1$ denotes a group of the formula $R_4$-CO- or $R_5R_6(OH)C$- or a carboxyl group, wherein $R_4$ and $R_5$ independently denote an alkyl group having 1–3 carbon atoms, and $R_6$ denotes a hydrogen atom or an alkyl group having 1–3 carbon atoms, $R_2$ denotes a hydrogen atom, an alkyl group having 1–5 carbon atoms or an alkyloxy group having 1–5 carbon atoms, $R_3$ denotes an alkyl group having 1–3 carbon atoms and n denotes 1–6 or a pharmaceutically acceptable acid addition salt thereof for preparing a pharmaceutical for improving dysuria, wherein 3,7-dihydro-3-methyl-1-(5-oxohexyl)-7-methyl-1H-purine-2,6-dione is excluded.

Representative of the xanthine derivatives used as an active ingredient in the pharmaceutical compositions for the improvement of dysuria according to the invention are 3,7-dihydro-3-methyl-1-(5-oxohexyl)-7-propyl-1H-purine-2,6-dione (formula II) or 3,7-dihydro-3-ethyl-1-(5-oxohexyl)-7-propyl-1H-purine-2,6-dione (formula III), 3,7-dihydro-3-methyl-1 -(4-oxopentyl)-7-propyl-1H-purine-2,6-dione (formula IV), 3,7-dihydro-3-methyl-1 -(4-carboxybutyl-7-propyl- 1H-purine-2,6-dione (formula V), 3,7-dihydro-3-methyl-1-(5-hydroxy-5-methylhexyl)-7-ethoxymethyl- 1H-purine-2,6-dione (formula VI), 3,7-dihydro-3-methyl-1-(5-hydroxymethyl)- 7-propyl-1H-purine-2, 6-dione (formula VII) and 3,7-dihydro-3-methyl- 1-(3-carboxypropyl)-7-propyl-1H-purine-2,6-dione (formula VIII), represented by chemical structural formulae II to VIII respectively.

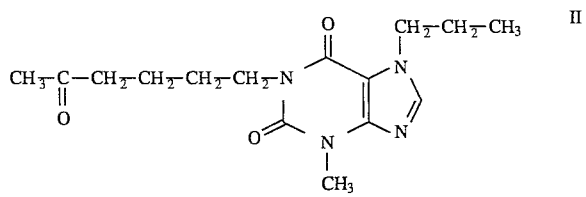

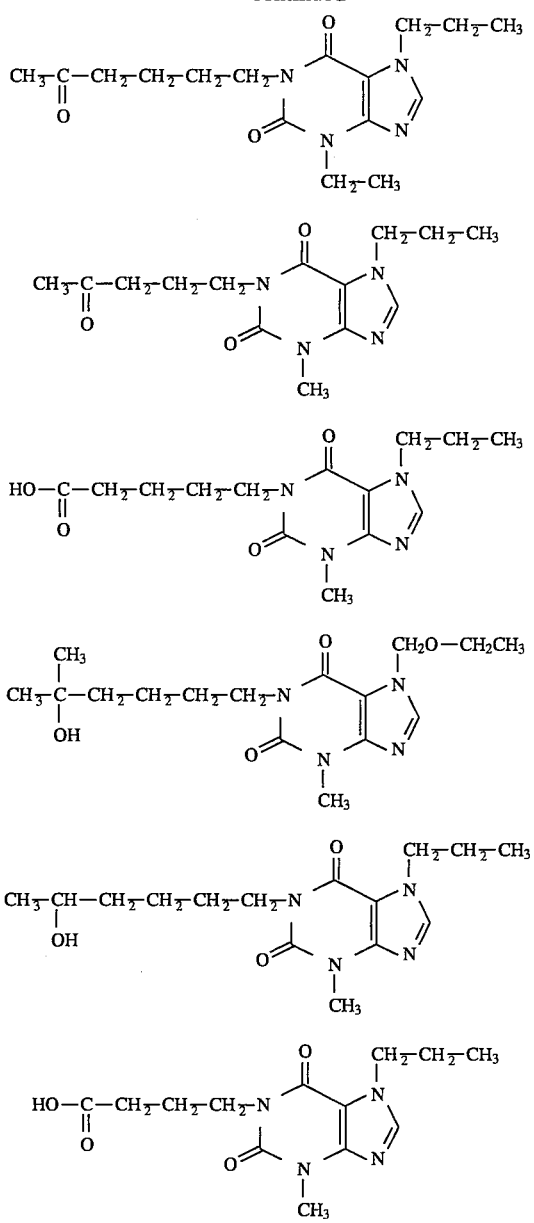

As the acid salts are mentioned, for example, mineral acid salts such as the hydrochloride, sulfate, hydrobromide and phosphate and organic acid salts such as the oxalate, acetate, lactate, succinate, citrate, tartrate, maleate, fumarate and malate.

Particularly, previous pharmacological studies report that the compound of formula II which is a substance named propentofylline possesses actions of improving cerebral circulation and metabolism, improving disturbed learning and memory, ameliorating cerebral edema, imroving the transformation ability of erythrocyte, etc. Furthermore, propentofylline has proved to be specifically active on vertebral artery which covers the brain in its return area and increase blood flow highly selectively during cerebral circulation (Japanese Patent Publication No. 33120/1977). It is therefore expected that propentofylline prompts improvement in the dysuria due to organic pathological changes of the brain such as cerebral infarction and hemorrhage as well as cerebral arteriosclerosis.

However, it is not reoprted that these xanthine derivatives are effective in the therapy of pollakiuria and incontinence of urine. We have found in animal experiments of the action on urination-reflexing constriction of the bladder that these xanthine derivatives induce prolongation of urination intervals and increase in the threshold of urination pressure, thus, marked increase in substantial volume of the bladder with almost no influence upon constrictive force of the bladder. Because of the increase in substantial volume of the bladder before urination, the xanthine derivatives according to the invention are of use in the therapy of pollakiuria and incontinence of urine.

The newly discovered pharmacological action of the inventive xanthine derivatives in the improvement of dysuria is believed to directly relax cystic smooth muscles due to its inhibitory actions of adenosine uptake as well as of cAMP and cGMP phosphodiesterase activities.

The route of administration of the inventive compounds can be oral, intravenous, subcutaneous, intramuscular and rectal. The compounds may be administered in the form of such formulations as tablet, sugar-coated tablet, pill, capsule, powder, granule, suppository and injection.

When orally administered it is preferable to give tablets, sugar-coated tablets, capsules or granules. In the case of parenteral administration injections or suppositories are preferably given.

The formulation for injections of the inventive compounds may be an injectable powdery formulation, for example. This formulation can be prepared by dissolving the compounds in water with addition of one or more appropriate water-soluble excipient such as mannitol, sucrose, lactose, maltose, glucose or fructose, dividing the solution into vials or ampules, lyophilizing and subsequently sealing them.

In addition to the ordinary forms of tablet, capsule, granule, fine granule and powder for oral administration, enteric formulations may also be employed.

In preparing the enteric formulations of the compounds a formulation is prepared first in an ordinary form such as tablet, granule or fine granule with addition of additives, as needed, including excipient such as mannitol, sucrose, lactose, realrose, starch, silicic acid anhydride and calcium phosphate, lubricants such as talc and magnesium stearate, binders such as carboxy methylcellulose, methylcellulose, gelatin and gum arabic and disintegrating agents such as calcium carboxymethylcellulose followed by coating with one or more enteric base materials such as cellulose acetate phthalate, hydroxypropylmethylcellulose phthalate, hydroxypropylmethylcellulose acetylsuccinate, polyvinyl alcohol phthalate, a styrene-maleic anhydride copolymer, a styrene-maleic acid copolymer, a methyl methacrylatemethacrylic acid copolymer, and a methyl acrylate-methacrylic acid copolymer, with addition of colorants such as titanium oxide as needed. In addition, the granules or fine granules prepared as above may be filled in capsules. Enteric capsules may also be prepared by coating ordinary capsules with the above-mentioned enteric base materials or by using capsules of the above-mentioned enteric base materials alone or in mixture with gelatin.

For suppository formulations of the compounds, a lipophilic base such as a semisynthetic base prepared from cacao butter or a fatty acid triglyceride(s) in mixture with a fatty acid monoglyceride(s) and/or a fatty acid diglyceride(s) in various proportions or a hydrophilic base such as polyethylene glycol or glycerogelatin is heated to a melt, which is then uniformly blended with the drug, and the blend is molded to give a suppository formulation.

Dosage in clinical use is usually 10–1000 mg of a xanthine derivative per dose in adults weighing 60 kg. Preferably, 30–300 mg of the drug is orally given three times a day.

Acute toxicity ($LD_{50}$) of propentofylline used in the invention was 1,150 mg/kg by oral administration and 180 mg/kg by intravenous administration in male rats, and 900 mg/kg by oral administration and 168 mg/kg by intravenous administration in male mice.

EXAMPLES

Examples are given below for demonstrating the effects of improving dysuria (pollakiuria and incontinence of urine) according to the invention. Effects of test drugs on urination-reflexing constriction of the bladder in anesthetized rats were examined according to Morikawa, et al. [in Oyo Yakuri/Pharmacometrics, Vol. 37, No. 1, pages 27–37, (1989)]. In the following examples, the bladder capacity designates the time from a urination to the next urination (urination interval), urination threshold pressure designates intracystic pressure) immediately prior to initiation of urination constriction and urination constriction pressure designates maximum internal pressure on urination constriction. Figures in the below table indicate relative level from the first and second reactions after administration of a drug taking the measured value before administration of the drug as 1 for bladder capacity (min.), urination threshold pressure (mmHg) and urination constriction pressure (mmHg), respectively.

EXAMPLE 1

Action of propentofylline (formula II) on urination-reflexing constriction of the bladder (Cystometrogram) in anesthetized rats-intravenous administration Groups of 4–6 SD male rats were used and each animal was subjected to laparotomy under anesthesia with urethan, ligature around the ureter and then exposure of the bladder, on the top of which was perforated with a small opening, through which a cannula with a three-way step cock was inserted.

One of the three-way stop cock was connected to a syringe for continuously introducing a physiological saline solution and another to a pressure transducer for the measurement of intrasystic pressure.

A physiological saline solution was introduced into the bladder at a rate of 55 μl per min., and changes in intracystic pressure were recorded until urination. From the intracystic pressure curve were determined bladder capacity, urination threshold pressure and urination constriction pressure to examine the action of the introduction of physiological saline solution.

The drug was given via a polyethylene tube inserted into the femoral vein. The results are shown in Table 1.

TABLE 1

Effects of intravenous administration of propentofylline on urination-reflexing constriction of the bladder

| Dose of propentofylline | No. of animals | Bladder capacity | | Urination threshold pressure | | Urination constriction pressure | |
|---|---|---|---|---|---|---|---|
| | | First | Second | First | Second | First | Second |
| Physiological saline solution | 4 | 1.0 ± 0.2 | 0.9 ± 0.2 | 1.0 ± 0.1 | 0.9 ± 0.1 | 1.1 ± 0.1 | 1.0 ± 0.1 |
| 0.2 mg/kg | 5 | 1.2 ± 0.8 | 1.1 ± 0.4 | 1.2 ± 0.5 | 1.0 ± 0.3 | 1.0 ± 0.1 | 0.9 ± 0.1 |
| 1 mg/kg | 5 | 2.5 ± 1.9 | 0.7 ± 0.2 | 1.1 ± 0.1 | 1.1 ± 0.2 | 1.0 ± 0.1 | 1.1 ± 0.2 |
| 5 mg/kg | 6 | 4.1 ± 2.6* | 1.0 ± 0.5 | 1.5 ± 0.4 | 1.2 ± 0.6 | 1.0 ± 0.1 | 1.0 ± 0.2 |
| 10 mg/kg | 5 | 3.5 ± 1.1* | 0.9 ± 0.5 | 2.1 ± 0.7** | 1.1 ± 0.3 | 1.0 ± 0.2 | 1.0 ± 0.2 |
| 20 mg/kg | 5 | 4.9 ± 3.2* | 1.0 ± 0.8 | 2.5 ± 0.8** | 1.5 ± 0.8 | 1.0 ± 0.1 | 1.0 ± 0.1 |

Each indicates mean ± standard deviation
**: $P < 0.01$
*: $P < 0.05$

EXAMPLE 2

Action of propentofylline (formula II) on urination-reflexing constriction of the bladder (Cystometrogram) in anesthetized rats-intraduodenal administration Groups of 4–5 SD male rats were fasted overnight and subjected to the same experimental procedures as in Example 1. The drug was given via a polyethylene tube inserted into the duodenum. The results are shown in Table 2.

TABLE 2

Effects of intraduodenal administration of propentofylline on urination-reflexing constriction of the bladder

| Dose of propentofylline | No. of animals | Bladder capacity | | Urination threshold pressure | | Urination constriction pressure | |
|---|---|---|---|---|---|---|---|
| | | First | Second | First | Second | First | Second |
| Physiological saline solution | 5 | 0.9 ± 0.5 | 1.1 ± 0.8 | 0.9 ± 0.2 | 0.9 ± 0.2 | 1.0 ± 0.1 | 1.0 ± 0.1 |
| 3 mg/kg | 4 | 1.1 ± 0.2 | 1.1 ± 0.3 | 1.0 ± 0.2 | 1.0 ± 0.2 | 1.1 ± 0.1 | 1.1 ± 0.2 |
| 10 mg/kg | 4 | 2.7 ± 1.8 | 1.0 ± 1.0 | 1.3 ± 0.3 | 1.3 ± 0.5 | 1.0 ± 0.1 | 0.9 ± 0.1 |
| 30 mg/kg | 5 | 2.7 ± 1.6 | 0.8 ± 0.6 | 1.6 ± 0.9 | 1.4 ± 0.9 | 0.9 ± 0.1 | 1.0 ± 0.1 |
| 50 mg/kg | 5 | 4.3 ± 2.1** | 0.6 ± 0.2 | 1.7 ± 0.6* | 1.4 ± 0.7 | 1.0 ± 0.1 | 1.0 ± 0.1 |

Each indicates mean ± standard deviation
**: $P < 0.01$
*: $P < 0.05$

EXAMPLE 3

Action of the compound of formulae VI on urination-reflexing constriction of the bladder (cystometrogram) in anesthetized rats-intravenous administration Groups of 4–5 SD male rats were subjected to the same experimental procedures as in Example 1. The results are shown in Table 3.

TABLE 3

Effects of intravenous administration of other xanthine derivatives on urination-reflexing constriction of the bladder

| Name and dose of the compound | No. of animals | Bladder capacity | | Urination threshold pressure | | Urination constriction pressure | |
|---|---|---|---|---|---|---|---|
| | | First | Second | First | Second | First | Second |
| Physiological saline solution | 4 | 1.0 ± 0.2 | 0.9 ± 0.2 | 1.0 ± 0.1 | 0.9 ± 0.1 | 1.1 ± 0.1 | 1.0 ± 0.1 |
| Compound VI 20 mg/kg | 5 | 1.8 ± 0.9 | 1.4 ± 1.0 | 1.3 ± 0.9 | 1.0 ± 0.4 | 1.0 ± 0.1 | 1.0 ± 0.1 |

Each indicates mean ± standard deviation

Preparation examples of the invention will be described below.

Preparation Example 1

To 20 g of propentofylline and 16 g of sodium chloride was added distilled water for injection to a total volume of 2,000 ml. The solution was sterile filtered through a Millipore Filter 0.22/ μ in pore size and divided into 5 ml ampules so as to contain 5 ml per ampule. The ampules were melt sealed and sterilized in an autoclave to prepare an injectable formulation.

Preparation Example 2

To 500 g of propentofylline were added 250 g of lactose, 150 g of corn starch, 150 g of calcium carboxymethyl cellulose, 42 g of talc, 5 g of magnesium stearate and 3 g of silicic acid anhydride. From the mixture were prepared tablets by conventional procedures. Separately, 40 g of hydroxypropylmethylcellulose, 2 g of Macrogol 6000, 3.5 g of titanium oxide and 3 g of talc were dispersed in 500 g of water. The tablets obtained above were coated with the aqueous dispersion to give tablets containing 115 mg of propentofylline per tablet.

As clearly seen from the results of the pharmacological tests described above, propentofylline in animal experiments on the action on urination-reflexing constriction of the bladder induces prolonged urination intervals and increased urination threshold pressure, that is, an increased substantial bladder capacity, with almost no influence upon constrictive force of the bladder, which suggest its effect of improving dysuria such as pollakiuria and incontinence of urine. In addition, it is characterized by safety.

What is claimed is:
1. A method for increasing bladder capacity in a patient in need of said increase which comprises administering a therapeutically effective amount of propentofylline (3,7-dihydro-3-methyl-1-(5-oxohexyl)-7-propyl- 1H-purine-2,6-dione) or a pharmaceutically acceptable acid addition salt thereof to said patient.
2. The method of claim 1, wherein said 3,7-dihydro-3-methyl-1-( 5-oxohexyl)-7-propyl-1H-purine-2,6-dione or a pharmaceutically acceptable acid addition salt thereof is in the form of a formulation for intravenous administration or a suppository.
3. The method of claim 1, wherein said 3,7-dihydro-3-methyl-1-( 5-oxohexyl)-7-propyl-1H-purine-2-6-dione or a pharmaceutically acceptable acid addition salt thereof is in the form of a formulation for oral administration.

* * * * *